(12) United States Patent
Seethapathy et al.

(10) Patent No.: US 10,444,201 B2
(45) Date of Patent: Oct. 15, 2019

(54) METHOD OF DETERMINING THE MAGNITUDE OF A FIELD VARIABLE OF AN ENERGY WAVE

(71) Applicant: ROLLS-ROYCE plc, London (GB)

(72) Inventors: Mani Seethapathy, Derby (GB); Sree Vamsi Tammineni, Wilmslow (GB); Stephen Samuel Wiseall, Derby (GB); David Cameron Wright, Loughborough (GB); Craig Brian Chapman, Manchester (GB); Pathmeswaran Raju, New Malden (GB)

(73) Assignee: ROLLS-ROYCE plc, London (GB)

( * ) Notice: Subject to any disclaimer, the term of this patent is extended or adjusted under 35 U.S.C. 154(b) by 520 days.

(21) Appl. No.: 14/929,817

(22) Filed: Nov. 2, 2015

(65) Prior Publication Data
US 2016/0139087 A1 May 19, 2016

(30) Foreign Application Priority Data

Nov. 18, 2014 (GB) .................................. 1420424.2

(51) Int. Cl.
*G01N 29/44* (2006.01)
*G01N 29/04* (2006.01)

(52) U.S. Cl.
CPC ....... *G01N 29/4472* (2013.01); *G01N 29/041* (2013.01); *G01N 2291/0289* (2013.01);
(Continued)

(58) Field of Classification Search
CPC ................................................. G01N 29/4472
See application file for complete search history.

(56) References Cited

U.S. PATENT DOCUMENTS

2002/0112540 A1* 8/2002 Zeroug .................. G01N 29/07
73/579

OTHER PUBLICATIONS

Banerjee S et al; "Controlled Space Radiation concept for mesh-free semi-analytical technique to model wave fields in complex geometries"; vol. 49, No. 8, Dec. 1, 2009; pp. 615-622; XP026740437.
(Continued)

*Primary Examiner* — John E Breene
*Assistant Examiner* — Jeffrey C Morgan
(74) *Attorney, Agent, or Firm* — Oliff PLC

(57) ABSTRACT

Determining magnitude of a field variable of an energy wave through domain of interest, including steps of: defining plurality of master-particles spaced within domain, master-particles being representative of field variables of energy wave at location of respective master-particle, and defining supporting domain $\Omega_m$ for each master-particle; computing field variables including position, magnitude and direction of propagation of each master-particle at predetermined time; defining plurality of virtual-particles within domain representative of magnitude of field variable of wave at location of respective virtual-particle; calculating magnitude $u_v$ of field variable of each virtual-particle at time of interest by applying formula:

$$u_v = \sum_{m=1}^{N} u_m f(q1) \times g(q2)$$

Where $v \in \Omega_m$ where N is total number of master-particles, $u_m$ is magnitude of respective master-particle, f(q1) is an envelope function relating magnitude of virtual-particle to distance from mas-
(Continued)

ter-particle in direction of propagation of master-particle, and g(q2) is a smoothing function.

6 Claims, 5 Drawing Sheets

(52) U.S. Cl.
CPC ............... *G01N 2291/0422* (2013.01); *G01N 2291/0423* (2013.01)

(56) References Cited

OTHER PUBLICATIONS

Jun. 3, 2016 Search Report issued in European Patent Application No. 15192518.

Wang et al., "An Improved Ray Tracing Algorithm for Ultrasonic CT in Nondestructive Inspections," IEEE, ICSP 2006 Proceedings.

Atkinson et al., "Algebraic Reconstruction Techniques for Tomographic Particle Image Velocimetry," 16th Australasian Fluid Mechanics Conference, Dec. 2-7, 2007, pp. 191-198.

Balvantin et al., "Ultrasonic Tomography Using Lamb Wave Propagation Parameters," 5th Pan American Conference for NDT, Oct. 2-6, 2011.

Okada et al., "A Ray Tracing Simulation of Sound Diffraction Based on the Analytic Secondary Source Model," IEEE Transactions on Audio, Speech, and Language Processing, Nov. 2012, vol. 20, No. 9, pp. 2448-2460.

Yamawaki, et al., "Numerical Calculation of Ultrasonic Propagation with Anisotropy," NDT&E International, Oct. 2000, vol. 33, No. 7, pp. 489-497.

Mares, "Simulation as a Support for Ultrasonic Testing," Journal of Modern Physics, 2014, vol. 5, pp. 1167-1172.

Sulsky et al., "Application of a Particle-in-Cell Method to Solid Mechanics," Computer Physics Communications, 1995, vol. 87, pp. 236-252.

O'Neill et al., "Ellipsis 3D: A Particle-in-Cell Finite-Element Hybrid Code for Modelling Mantle Convection and Lithospheric Deformation," Computers & Geosciences, 2006, vol. 32, pp. 1769-1779.

Verleye et al., "Implementation of a 2D Electrostatic Particle-in-Cell Algorithm in Unified Parallel C with Dynamic Load-Balancing," Computers & Fluids, 2013, vol. 80, pp. 10-16.

Brackbill et al., "Flip: A Low-Dissipation, Particle-in-Cell Method for Fluid Flow," Computer Physics Communications, 1998, vol. 48, pp. 25-38.

Pukhov et al., "Relativistic Laser-Plasma Interaction by Multi-Dimensional Particle-in-Cell Simulations," Physics of Plasmas, May 1998, vol. 5, No. 5, pp. 1880-1886.

Innocenti et al., "A Multi Level Multi Domain Method for Particle In Cell Plasma Simulations," Journal of Computational Physics, 2013, vol. 238, pp. 115-140.

Jun. 2, 2015 Search Report issued in British Patent Application No. 1420424.2.

\* cited by examiner

METHOD OF DETERMINING THE MAGNITUDE OF A FIELD VARIABLE OF AN ENERGY WAVE

FIELD OF THE INVENTION

The present invention relates to a method of simulating wave propagation in a medium, and particularly but not exclusively to a method of simulating ultrasound propagation through a candidate metallic preform shape to determine whether the metallic preform shape is inspectable by ultrasonic testing.

BACKGROUND TO THE INVENTION

Waves such as electromagnetic, seismic and acoustic waves propagate through media in a predictable way in accordance with well understood physical principles. However, directly determining wave propagation through a medium having complex boundaries in accordance with physical laws is computationally expensive.

In one example, it may be desirable to perform non-destructive testing (NDT) in the form of ultrasonic testing on a workpiece to ensure that no defects such as inclusions are present in the raw material prior to carrying out further machining. FIG. 1 shows a cross sectional view through part of a forging 10 for a turbine disc of a gas turbine engine. The turbine disc is annular, having a shape shown in FIG. 2. The forging 10 includes an initial workpiece profile 12 (also known as a "Condition of Supply", or COS) which is machined from a larger forging geometry 10. The workpiece 12 comprises a polygon having rectilinear sides. The workpiece 12 is further machined to form a final profile 14, which is the required shape of the turbine disc. Before the workpiece 12 is further machined, the workpiece 12 is placed within an ultrasonic inspection apparatus 15 shown in FIG. 2. The apparatus 15 contains sound conducting media such as water 16 which has a different refractive index than the workpiece 12 due to the lower speed of sound in water. An ultrasonic transducer 18 is used to perform ultrasonic testing on the workpiece 12 to determine whether parts of the final profile 14 which will be subject to high stresses include any defects.

In order to inspect the workpiece 12 to the satisfaction of regulatory authorities, it must be shown that any high stress regions in the final profile 14 can be subjected to three separate ultrasonic testing passes per side of the workpiece profile 12. When designing the workpiece profile 12 therefore, NDT requirements require that at least any high stress areas in the final profile 14 can be tested from angles defined by the external profile of the workpiece 12.

In particular, it must be shown that a defect in some locations, and particularly within high stress regions, can be detected using a NDT technique such as ultrasonic testing. Consequently, it is desirable to be able to model the COS 12 to show that a defect in a given area can be detected, i.e. that a defect in the region of interest is detectable.

Methods are known for simulating wave propagation in order to, for instance, model ultrasonic testing of an article. On a physical level, wave propagation is governed by a wave equation, which is a partial differential equation. Methods for solving this equation to simulate wave propagation across a domain of interest over time include methods such as the Finite Difference Method (FDM), and the Finite Element Method (FEM). FDM and FEM are known as "meshed" methods, and operate by discretising the problem domain into a plurality of sub-domains (or cells) known as a mesh. In the case of FDM, the differential operators in the wave equations are replaced with the difference approximations from the Taylor series. A further wave based method comprises the Boundary Element Method (BEM).

"Meshless" methods are also known, such as the Distributed Point Source Method (DPSM). In this method, the transducer face and interfaces are modelled as distributed point sources. The field variables of the ultrasonic wave are computed using Green's function. Based on Green's function, an arbitrary point in space will be influenced by the distributed points surrounded by it. Mesh free methods are preferable in some situations to meshed methods, as they have high computational efficiency. One type of Meshless method is known as a "Domain type" method. In Domain type methods, the differential equations are approximated at the boundary as well as in the domain. Strong or weak formulations of the wave equation are used in the domain area, as this type of solution is well behaved in the domain. However, in known methods, singularities (i.e. errors in the computation) occur at boundaries as well as at defect areas, making it difficult to distinguish boundaries from defects in the model.

In each case however, there is a compromise between wave propagation simulation accuracy and computational expense, as more accuracy generally leads to longer computational time required to carry out the calculation. Other methods include geometrical methods such as ray tracing, the Image Source Method and beam tracing. However, while faster, such geometrical methods are less accurate.

Consequently, there is a desire to provide a new method of simulating wave propagation through media such as metals in order to, for example, determine the available scan coverage of an article. Such a method must be computationally efficient, as well as highly accurate. The present invention seeks to provide such a method.

SUMMARY OF THE INVENTION

According to a first aspect of the present invention, there is provided a computer implemented method of determining the magnitude of a field variable of an energy wave at a predetermined time through a domain of interest, the method comprising the steps of:

defining a plurality of master particles spaced within the domain, the master particles being representative of field variables of an energy wave at the location of the respective master particle, and defining a supporting domain $\Omega_m$ for each master particle;

computing field variables including the position, magnitude and direction of propagation of each master particle at the predetermined time;

defining a plurality of virtual particles spaced within the domain representative of the magnitude of a field variable of the wave at the location of the respective virtual particle;

calculating a magnitude $u_v$ of the field variable of each virtual particle at the time of interest by applying the formula:

$$u_v = \sum_{m=1}^{N} u_m f(q1) \times g(q2)$$

Where $v \in \Omega_m$

Where N is the total number of master particles, $u_m$ is the magnitude of a respective master particle, f(q1) is an envelope function relating the magnitude of the virtual particle to the distance from the master particle in the direction of propagation of the master particle, and g(q2) is a smoothing function relating the magnitude of the virtual particle to the distance from the master particle normal to the direction of propagation of the master particle.

Accordingly, the invention provides a method of determining wave propagation through a domain of interest by considering the position, magnitude and direction of the wave as the wave propagates through the domain, then only calculating the wave superposition aspect of the wave equation at the time of interest, without the requirement for calculating preceding time intervals. Consequently, the accuracy of the method is high, while the computational efficiency is also high, since the density of the virtual points does not determine the accuracy of the computation of the position, magnitude and direction of the wave fronts.

The energy wave may comprise one of an acoustic wave such as an ultrasonic wave, an electromagnetic wave, a seismic wave The acoustic wave type may comprise one or more of a longitudinal waves, Sholte wave (interface waves), Rayleigh wave, shear wave, Stonley waves and Love wave.

The supporting domain $\Omega_m$ may comprise an ellipse having a first axis (q1) in the direction of propagation of the master particle, and a second axis (q2) in a direction normal to the propagation of the master particle. The length of the first axis q1 may comprise the wavelength of the energy wave, or may comprise the pulse length of the energy wave. The length of the second axis q2 may comprise the distance between neighbouring master particles.

Each of the envelope function and the smoothing function may comprise any one of a Gaussian function, a linear smoothing function, and a moving average smoothing function.

According to a second aspect of the invention, there is provided a method of determining the detectability of a defect within a supplied part out of which a final component is to be machined, the method including the steps of:

defining a domain of interest representative of the supplied part;

defining a simulated defect within the domain of interest;

determining the magnitude of a field variable of an energy wave at a receiver location within the domain of interest at a predetermined time in accordance with the first aspect of the invention;

wherein the defect is determined to be detectable where an energy wave reflected by the defect has a field variable magnitude greater than a predetermined amount when received by the receiver.

Advantageously, the method provides a method of simulating whether a defect can be detected by reflecting an energy wave from a defect, for a defect in a given location in a modelled domain of interest. Consequently, the method can be used to prove that any defects within the modelled domain of interest are detectable, thereby ensuring that defects do not go undetected during acceptance testing.

Further aspects of the invention provide: a computer program comprising code which, when run on a computer, causes the computer to perform the method of the first or second aspect; a computer readable medium storing a computer program comprising code which, when run on a computer, causes the computer to perform the method of the first or second aspect; and a computer system programmed to perform the method of the first or second aspect.

Features of the first aspect of the invention can be used in the second aspect of the invention where appropriate.

DETAILED DESCRIPTION

Figure 1:
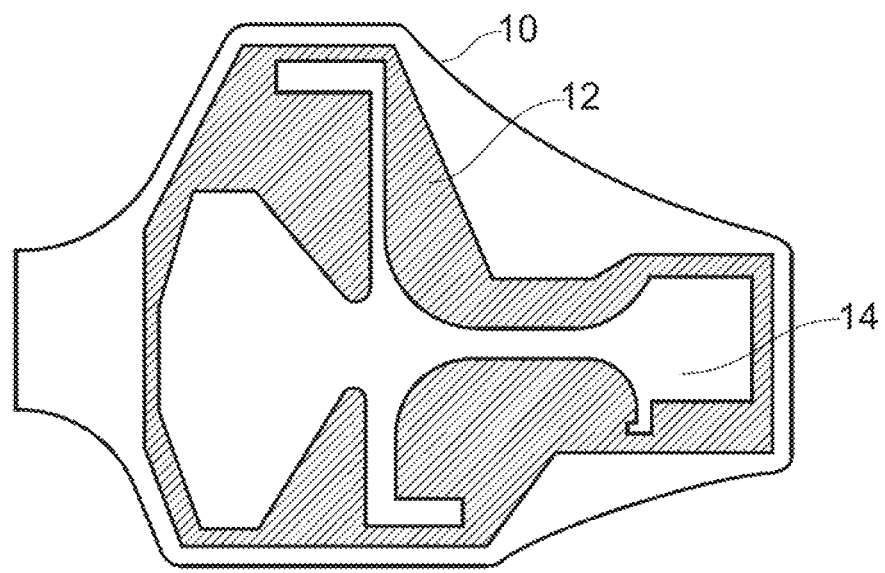
FIG. 1 shows a cross sectional view through a casting suitable to for producing a rotor disc of a gas turbine engine.
Figure 2:
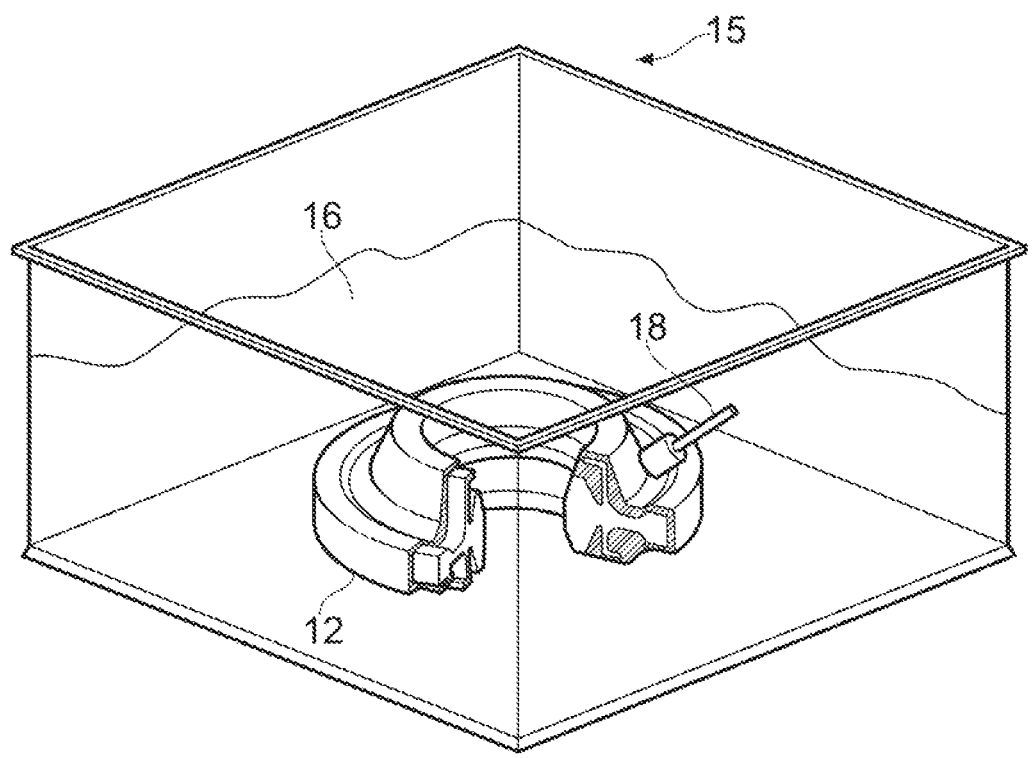
FIG. 2 shows an perspective view of an inspection arrangement.
Figure 3:
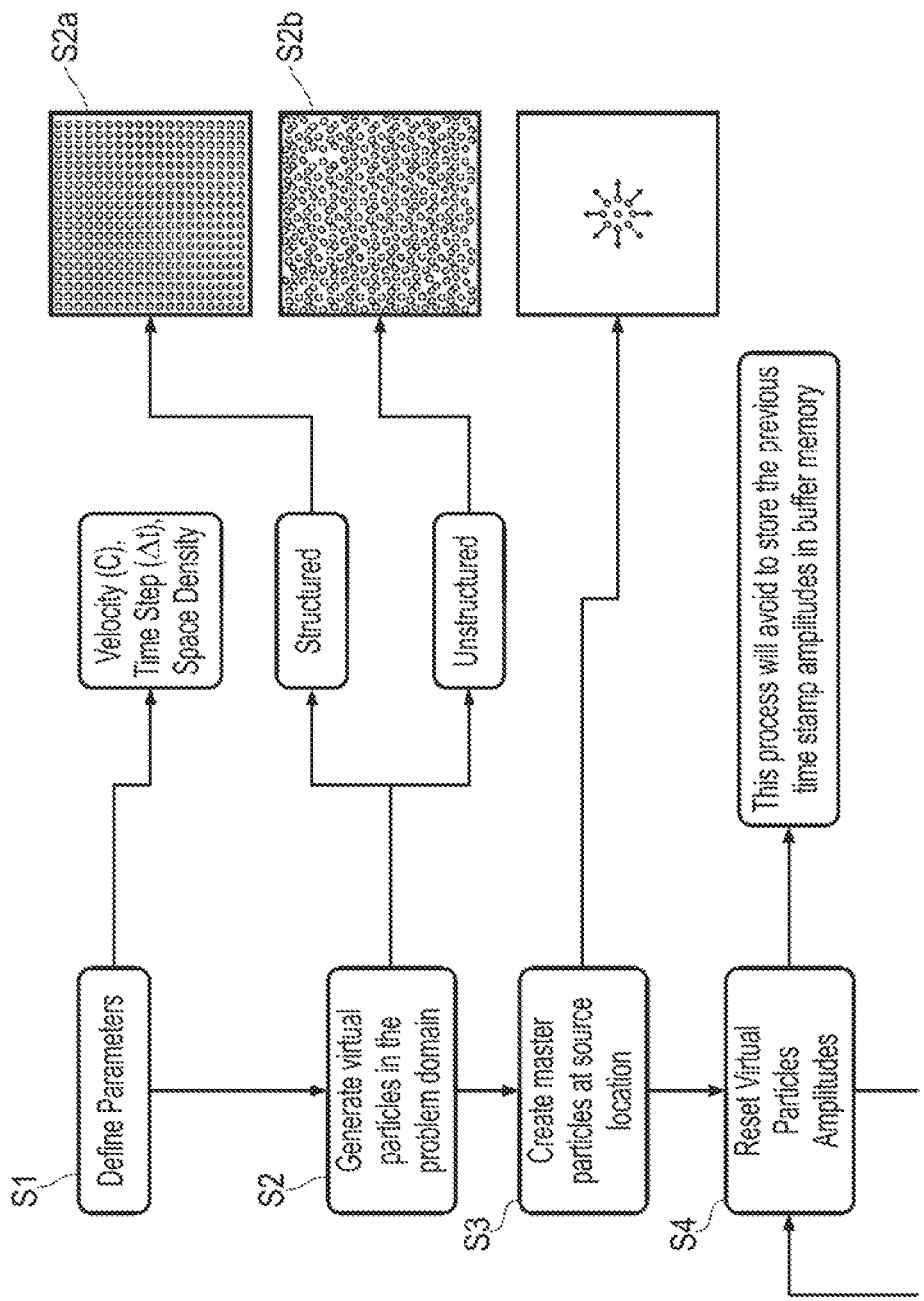
FIG. 3 shows a flow diagram illustrating a method in accordance with the present disclosure.
Figure 3:
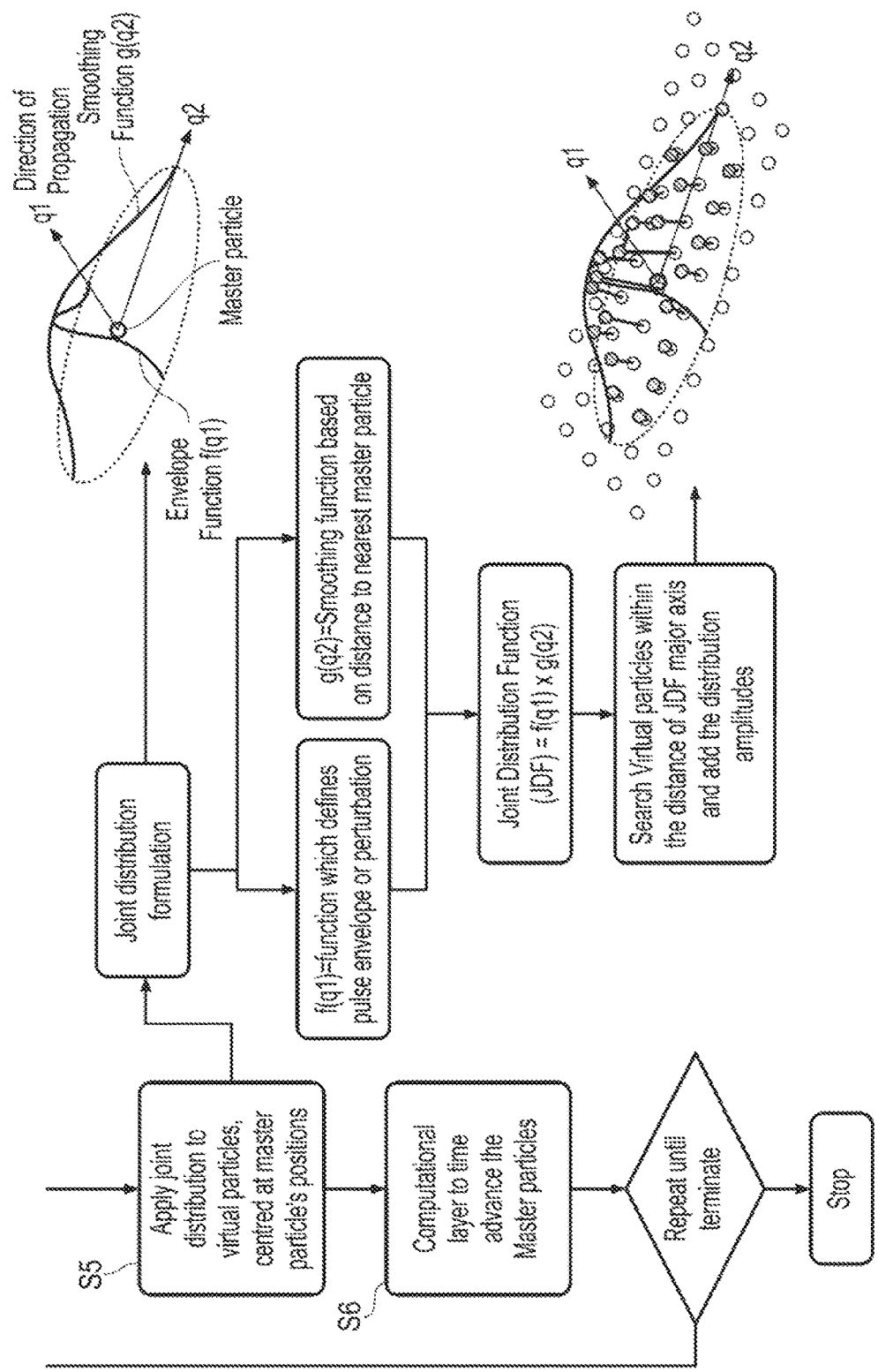

FIG. 3 shows steps in a method of determining the magnitude of a field variable of an energy wave propagating through a medium with respect to time in accordance with the present disclosure. Example results of this simulation are shown in FIGS. 4a to 4c.

In a first step S1, parameters of the process are defined. These parameters include the velocity of the energy wave in question in the simulated medium (for example, the speed of sound c in the medium where the wave is a sound wave), as well as the initial amplitude of the wave, and the initial wavelength of the energy wave. Where the medium is anisotropic (i.e. the speed of sound c is dependent on the direction of travel), this parameter may comprise a direction dependent function. Further parameters include a desired temporal resolution (i.e. the difference in time Δt between time steps) and spatial resolution of master and virtual particles (which will be explained in greater detail hereafter).

In step S2, a problem domain is defined. The problem domain comprises a geometrical representation of an article such as the COS 12 to be investigated, comprising a shape bounded by walls. The shape may comprise a rectilinear shape, comprising straight lines to bound the domain of interest. A plurality of spaced points in the form of "virtual particles" are defined in the problem domain, in either a regular pattern as shown in step S2a, or in a randomly or pseudo-randomly generated irregular pattern, as shown in step S2b. Each virtual particle represents the magnitude of a desired field variable (such as material perturbation caused by the sound wave in the case of an ultrasonic sound wave) at the location within the problem domain of the respective virtual particle.

In step S3, a plurality of master particles are defined. Each master particle represents field variables including at least the position, magnitude and direction of propagation of a wave front originating from a wave source. At time T=0, the master particles are located at the origin of the wave source and may have either a radial propagation or linear propagation direction depending on the type of wave being modelled (i.e. a radial or linear wave front). The example shown in FIG. 3 illustrates a radially propagating wave. At time T=0, the magnitude of the field variables is set as a series of parameters, in accordance with the wave source to be simulated. For example, where the simulation is of an ultrasonic wave, the field variables are set as those of the incoming wave from the transducer 18.

Each master particle further comprises a supporting domain $\Omega_m$, which defines a region of the problem domain in which in which the magnitude of the master particle is to be distributed to the virtual particles. In the example shown in FIG. 3, the supporting domain $\Omega_m$ comprises an ellipse having a first axis q1 extending in a direction of propagation of the master particle, and a second axis q2 extending in a direction normal to the direction of propagation of the master particle. The length of the first axis q1 could comprise the wavelength of the energy wave (as defined in step S1 or calculated in accordance with step S6, described below). In the case of ultrasonic waves having a high frequency, the first axis could comprise the pulse length of the wave. The second axis q2 comprises the distance between respective master particle and an adjacent master particle, as defined by the master particle spatial resolution defined in step S1 for the case of time step T=0.

In step S5, the magnitude $u_v$ of each of the virtual particles in the problem domain is calculated in accordance with the following formula:

$$u_v = \sum_{m=1}^{N} u_m f(q1) \times g(q2) \quad \text{(Formula 1)}$$

Where $v \in \Omega_m$

In formula 1, N is the total number of master particles within the domain of interest, $u_m$ is the magnitude of a respective master particle for the field variable of interest (as determined by the parameters set in step S1 for time t=0, or in step S6 as described below for subsequent time steps), f(q1) is an envelope function relating the magnitude of the virtual particle to the distance from the respective master particle in the direction of propagation of the respective master particle (i.e. axis q1), and g(q2) is a smoothing function relating the magnitude of the virtual particle to the distance from the respective master particle normal to the direction of propagation of the master particle (i.e. axis q2). The product of f(q1) and g(q2) is referred to hereafter as the "joint distribution function". The above is calculated where v is a member of (i.e. located within) a supporting domain $\Omega_m$ of a master particle.

The envelope function could comprise any of a Gaussian function, a linear smoothing function, and a moving average smoothing function. Essentially, the envelope function represents the distribution of wave intensity through its wavelength, which in mode cases is essentially a Gaussian distribution. In this example, where the energy wave comprises an ultrasonic wave, the envelope function f(q1) and smoothing function g(q2) could be of the form $$f(q1) = e^{\frac{(y_m - y_v)^2}{2 * \text{wavelength of pulse}^2}}$$

$$g(q2) = e^{\frac{(x_m - x_v)^2}{2 * \text{smoothing distance}^2}}$$

Where, master particles' co-ordinate $(x_m, y_m)$ and virtual particles' co-ordinate $(x_v, y_v)$ are measured with respect to moving frame (q1, q2) of respective master particle.

Figure 4:
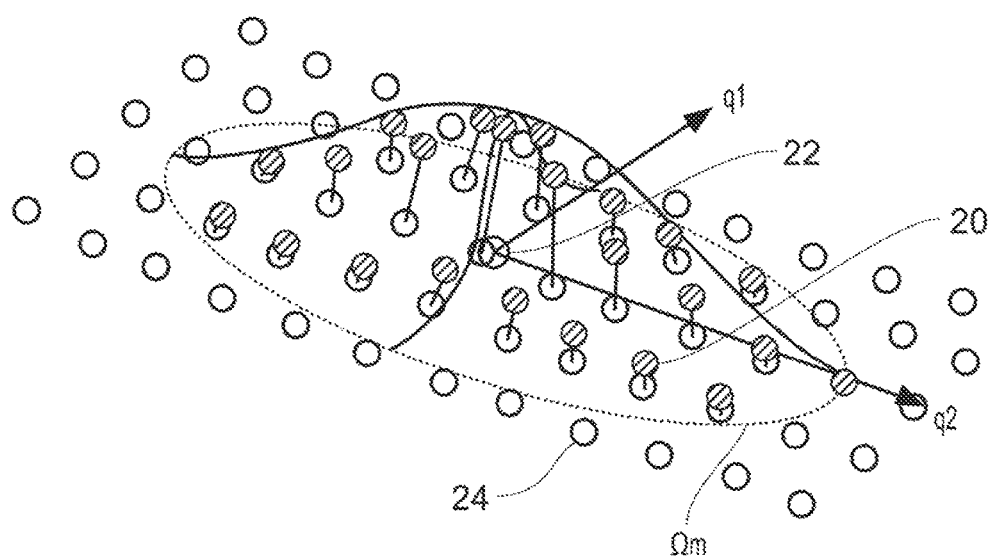
FIG. 4 shows a visualisation of calculated magnitudes of a wave propagating through a medium.
Figure 5A:
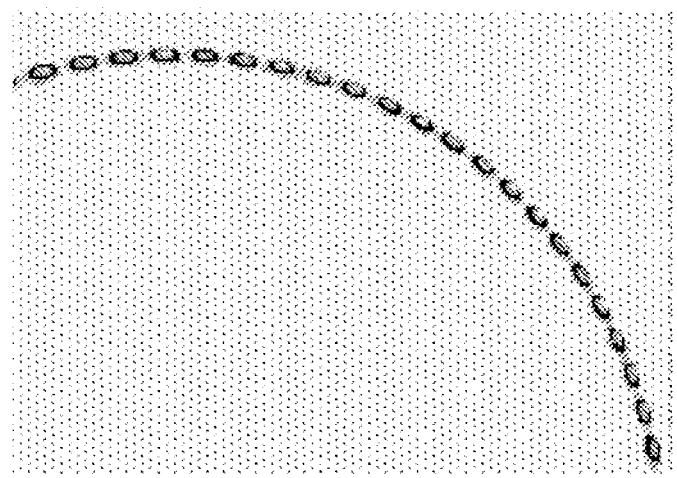
FIGS. 5a to 5c show an output of a method in accordance with the method of FIG. 3.
Figure 5B:
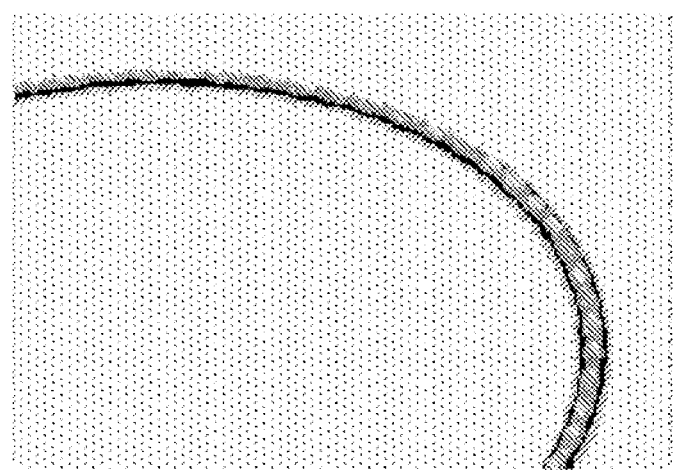
Figure 5C:
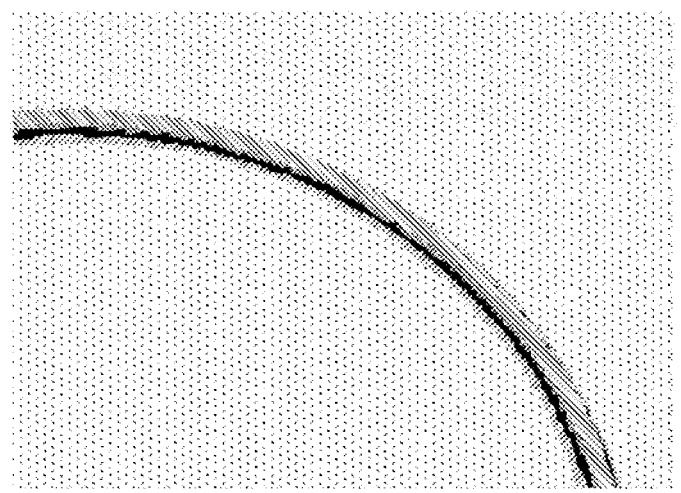

FIG. 4 shows a worked example of calculated magnitudes for virtual particles 20 within the supporting domain $\Omega_m$ of a single master particle 22. In FIG. 4, the magnitude of the virtual particles is represented by the height of each particle above the plane of surrounding virtual particles 24, which lie outside the supporting region $\Omega_m$. as can be seen, the magnitude of the master particle 22 is distributed to the surrounding virtual particles 24 within the supporting region $\Omega_m$.

In step S4, the magnitudes of the virtual particles is reset to zero. Consequently, the memory requirements of the described method is reduced relative to prior methods, since the magnitudes of field variables in previous time steps does not have to be maintained in memory.

At a given time step, the joint distribution function is applied to the virtual particles 20 within the supporting region $\Omega_m$ for each master particle 22. As can be seen from FIG. 4, the magnitude of the virtual particles 20 at each location is a function of the product of the envelope function and the smoothing function for the location of each virtual particle 20.

Referring again to FIG. 3, at step S6, the time is advanced by Δt, and the new field variables for the master particles are calculated. These field variables include the position, magnitude and direction of propagation of the wave at the location of the respective master particle.

There are a number of ways in which the field variables can be calculated. In one example, the field variables are calculated by taking into account the effects of advection, spreading, reflection/refraction.

For example, the propagation could be determined in accordance with a geometrical method such as ray tracing method, or by a wave based method. In the ray tracing method, the acoustic source is modelled as emitting a large number of rays (lines or particles) based on its directivity pattern. The number of rays in each direction is decided stochastically. The specular reflections are computed for each wall of the domain. Computational complexity of propagation depends on the number of walls present in the domain.

Normally for isentropic materials, the propagation of the ray path follows a straight line due to the homogeneity of material structure. Time of flight (TOF) is the measure of standard time taken to propagate through the ray paths. In general, TOF for the ray travelling along straight line of length (L) can be evaluated using $$TOF = \int_L \frac{dl}{c}$$

In case of an anisotropic material or interfaces with dissimilar materials, the resultant ray path tends to bend. This phenomenon of the ray occurs difference in propagation velocity between the two material. The resulting TOF can be computed by applying slowness (S(x, y)) distribution to original TOF formula.

$$TOF = \int_L S(x,y) dl$$

Wang et al., (2006) demonstrated the computation of slowness distribution for a bent ray path. Specifically for bent rays, computational performance and accuracy of the field variables depend exclusively on the reconstruction techniques used to integrate all available rays. In the literature, there were several algebraic reconstruction techniques (ART) available to improve the performance and accuracy of the field image. Atkinson and Soria (2007), compared various types of ART and their findings suggests that the multiplicative algebraic reconstruction technique (MART) provides greater accuracy. Wang et al., implemented MART ray tracing algorithm in bend ray computation and its comparison with numerical simulation produces good accuracy. Later study of Balvantin and Baltazar (2011) confirms the accuracy of MART algorithm. Usually the ray tracing produced specular reflections in the walls of domain. In reality the walls tend to spread the sound around the incident area and cause the scattered wave field. In ray tracing, to transform specular into scattered rays, methods like Monte Carlo integration are used to sample the number of scattered rays (Okada et al., 2012).

The above method can be used to assess the detectability of a defect within the domain of interest by ultrasonic waves transmitted and detected by the transducer 18.

In a first step, the domain of interest COS 12 is defined, along with a wave source location corresponding to a candidate location of the transducer. A test defect 26 is introduced in an area of interest, and the following method is used to determine whether the defect 26 can be detected from the candidate transducer location.

The propagation of the ultrasonic wave from the transducer 18 is computed using the above described ray tracing method (or another known computational method), by modelling the test defect 26 as a source of reflection within the domain. A time T at which reflect waves are returned to the transducer 18 is determined. The above described method of the first aspect of the invention is used to determine the amplitude of the signal at the time T at the candidate location of the transducer 18. This is compared with a predetermined transducer sensitivity—if the amplitude of the signal exceeds the predetermined transducer sensitivity, the defect is determined to be detectable from the candidate transducer location. If the signal does not exceed the predetermined transducer sensitivity, then the transducer is relocated to a new candidate location. If, after exhausting candidate transducer locations, the defect 26 cannot be detected from any accessible locations, then the defect 26 is deemed to be undetectable, and the geometry may have to be redesigned.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For example, the position of the wavefront could be determined using methods other than ray tracing, such as by the "Origami Method" outlined in applicant's co-pending GB patent application titled "Method of Determining Wave Propagation in a Medium".

Aspects of any of the embodiments of the invention could be combined with aspects of other embodiments, where appropriate.

The invention claimed is:

1. A computer implemented method of determining the detectability of a defect within a supplied part out of which a final component is to be machined, the method comprising the steps of:
    defining a domain of interest representative of the geometry of the supplied part having a simulated defect;
    defining a plurality of master particles spaced within the domain, the master particles being representative of field variables of an energy wave at the location of the respective master particle, and defining a supporting domain $\Omega_m$ for each master particle;
    computing field variables including the position, magnitude and direction of propagation of each master particle at a predetermined time step;
    defining a plurality of virtual particles spaced within the domain representative of the magnitude of a field variable of the wave at the location of the respective virtual particle;
    calculating a magnitude of the field variable of each virtual particle at the time of interest by applying the formula:

$$u_v = \sum_{m=1}^{N} u_m f(q1) \times g(q2)$$

Where $v \in \Omega_m$ where N is the total number of master particles, $u_m$ is the magnitude of a respective master particle, $f(q1)$ is an envelope function relating the magnitude of the virtual particle to the distance from the master particle in the direction of propagation of the master particle, and $g(q2)$ is a smoothing function relating the magnitude of the virtual particle to the distance from the master particle normal to the direction of propagation of the master particle;
    determining the magnitude of a field variable of a virtual particle located at a receiver location within the domain of interest at a predetermined time;
    wherein the defect is determined to be detectable where virtual particle located at a receiver location within the domain of interest at a predetermined time has a field variable magnitude greater than a predetermined amount.

2. A method according to claim 1 wherein the energy wave comprises one of an acoustic wave, an electromagnetic wave, or a seismic wave, wherein the acoustic wave type may comprise one or more of a longitudinal waves, Sholte wave (interface waves), Rayleigh wave, shear wave, Stonley waves and Love wave.

3. A method according to claim 1, wherein the supporting domain $\Omega_m$ comprises an ellipse having a first axis in the direction of propagation of the master particle, and a second axis in a direction normal to the propagation of the master particle.

4. A method according to claim 3, wherein the length of the first axis comprises the wavelength of the energy wave, or may comprise the pulse length of the energy wave.

5. A method according to claim 3, wherein the length of the second axis comprises the distance between neighbouring master particles.

6. A method according to claim 1, wherein each of the envelope function and the smoothing function comprises any one of a Gaussian function, a linear smoothing function, and a moving average smoothing function.

* * * * *